United States Patent [19]
Jaeggi

[11] Patent Number: 5,804,731
[45] Date of Patent: Sep. 8, 1998

[54] ULTRASONIC DEVICE FOR MEASURING THE INTERNAL DEFECTS OF A RAIL

[75] Inventor: Jean-Pierre Jaeggi, Geneva, Switzerland

[73] Assignee: Speno International SA, Geneva, Switzerland

[21] Appl. No.: 839,179

[22] Filed: Apr. 23, 1997

[30] Foreign Application Priority Data

Nov. 25, 1996 [CH] Switzerland ............................ 2898/96

[51] Int. Cl.⁶ .......................... G01N 29/12; G01N 29/26
[52] U.S. Cl. .................................. 73/636; 73/620; 73/624
[58] Field of Search .............................. 73/620, 636, 634, 73/624, 625, 635, 639, 641; 33/1 Q, 287, 523.1, 523.2, 651.1

[56] References Cited

U.S. PATENT DOCUMENTS

| | | | |
|---|---|---|---|
| 2,992,553 | 7/1961 | Joy | 73/636 |
| 3,028,751 | 4/1962 | Joy | 73/634 |
| 3,028,753 | 4/1962 | Joy | 73/636 |
| 3,251,220 | 5/1966 | Joy | 73/620 |
| 3,768,306 | 10/1973 | Stearns | 73/625 |
| 3,960,005 | 6/1976 | Vezina | 73/625 |
| 4,593,569 | 6/1986 | Joy | 73/636 |
| 4,689,995 | 9/1987 | Turbe | 73/636 |
| 4,700,574 | 10/1987 | Turbe | 73/636 |
| 5,020,371 | 6/1991 | Panetti | 73/636 |
| 5,522,265 | 6/1996 | Jaeggi | 73/625 |

Primary Examiner—Hezron E. Williams
Assistant Examiner—Rose M. Miller
Attorney, Agent, or Firm—Young & Thompson

[57] ABSTRACT

An ultrasonic device for continuously detecting and/or measuring in situ internal defects of a railway rail includes at least one ultrasonic sensor (15) subjected to a pressure tending to move it in the direction of the rail. The sensor presses against the rail through a smooth web 17 made of a synthetic material that is pervious to ultrasounds.

16 Claims, 4 Drawing Sheets

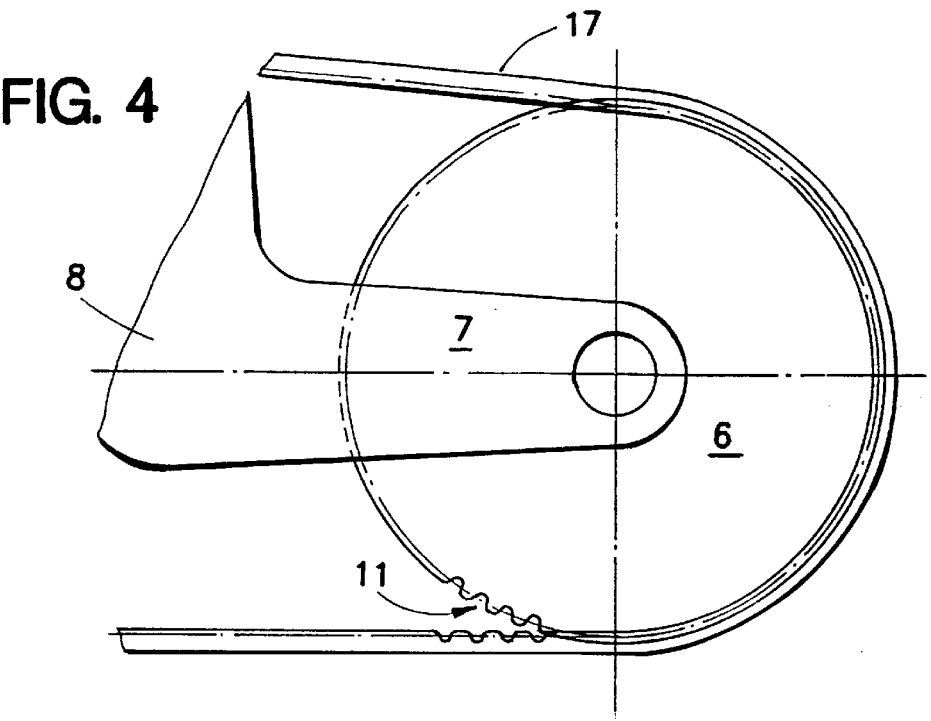
FIG. 4
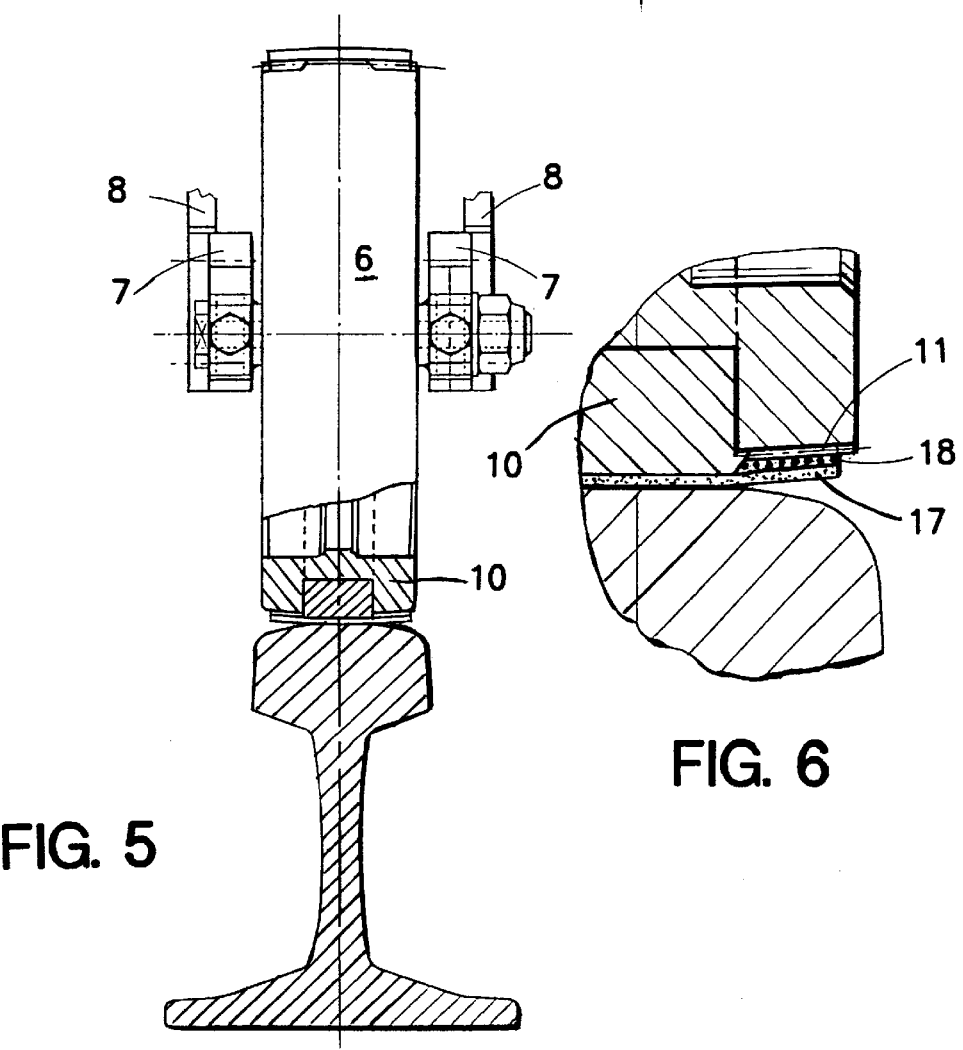
FIG. 5
FIG. 6

ULTRASONIC DEVICE FOR MEASURING THE INTERNAL DEFECTS OF A RAIL

The present invention is concerned with a device for measuring or detecting the internal defects of the rails of a railway and, more particularly, an ultrasonic device adapted to operating continuously on rails. Devices for analysing a body by means of a beam of ultrasounds are well known and are used for the detection and the measuring of internal defects of the rails of a railway, either continuously in situ, or in a workshop. According to this principle, a beam of ultrasounds is emitted in the direction of the rail from a sensor placed on the upper surface of a rail, the energy is reflected by the rail and its internal defects are then detected and measured by appropriate electronic circuits. The patents U.S. Pat. No. 4,689,995, U.S. Pat. No. 4,700,574 and EP 0374395 describe measurement methods and devices for their implementation.

To obtain a reliable measurement, it is essential to ensure a good acoustic contact between the sensor and the rail. The geometrical position of the rail is never perfect and a poor alignment of the rail, the localized deformations the rails and the discontinuities of the rail, for example at junctions, make the sensors jump on the rail, which results in the loss of the acoustic contact and obviously causes perturbations in the detection and the measuring of the defects of the rails. These perturbations are all the more important as the speed of the vehicle carrying the sensors increases.

The existing measuring carriages of this type include up to half a dozen sensors per length of rail for allowing a complete verification of all the defects of the rail. These sensors are generally carried by a common beam driven and guided along the rail by appropriate means. Owing to the mass and the length of this beam, it is extremely difficult, if not impossible, to ensure at all times a perfect sensor-rail contact, so that these devices can only be operated at speeds which are limited to low values, lesser than 20 km/hr for example.

Measuring devices have been developed such as those described in the patent U.S. Pat. No. 5,522,265 in which the sensors are placed in the housings of a shoe and are movable vertically with respect to this shoe while being applied against the surface of the rail by a determined force. This prevents the sensor from bouncing away from the rail and improves the acoustic contact between the sensors and the rail. The result thereof is that the speed of operation can be increased.

However, with such devices, the sensors remain in direct contact with the rail and, accordingly, they are subject to an important wear and can be damaged seriously by burrs or larger undulations on the surface of the rail. Thus, the useful life of such sensors is very short and they must be changed frequently, which entails high costs and work stoppages, both long and frequent.

Accordingly, the present invention is aimed at providing an ultrasonic device for detecting and/or measuring the internal defects of the rails of a railway, which device can be driven at high speed along the railway to be measured and of which the ultrasonic sensors are protected from impacts and from the roughness of the surface of the rail head, in such a manner as to significantly improve their reliability and increase their useful life. Another purpose of the present invention is to increase the reliability and the accuracy of detection and measuring of the internal defects of the rails monitored.

The drawings illustrate schematically and by way of example an embodiment of the device according to the invention.

FIG. 4 is a detailed view showing at an enlarged scale the meshing of a strap with a roller.

FIG. 5 is a partially cross-sectional view at an enlarged scale, taken along line V—V of FIG. 1.

FIG. 6 is a detail of FIG. 5, at an enlarged scale.

Figure 1:
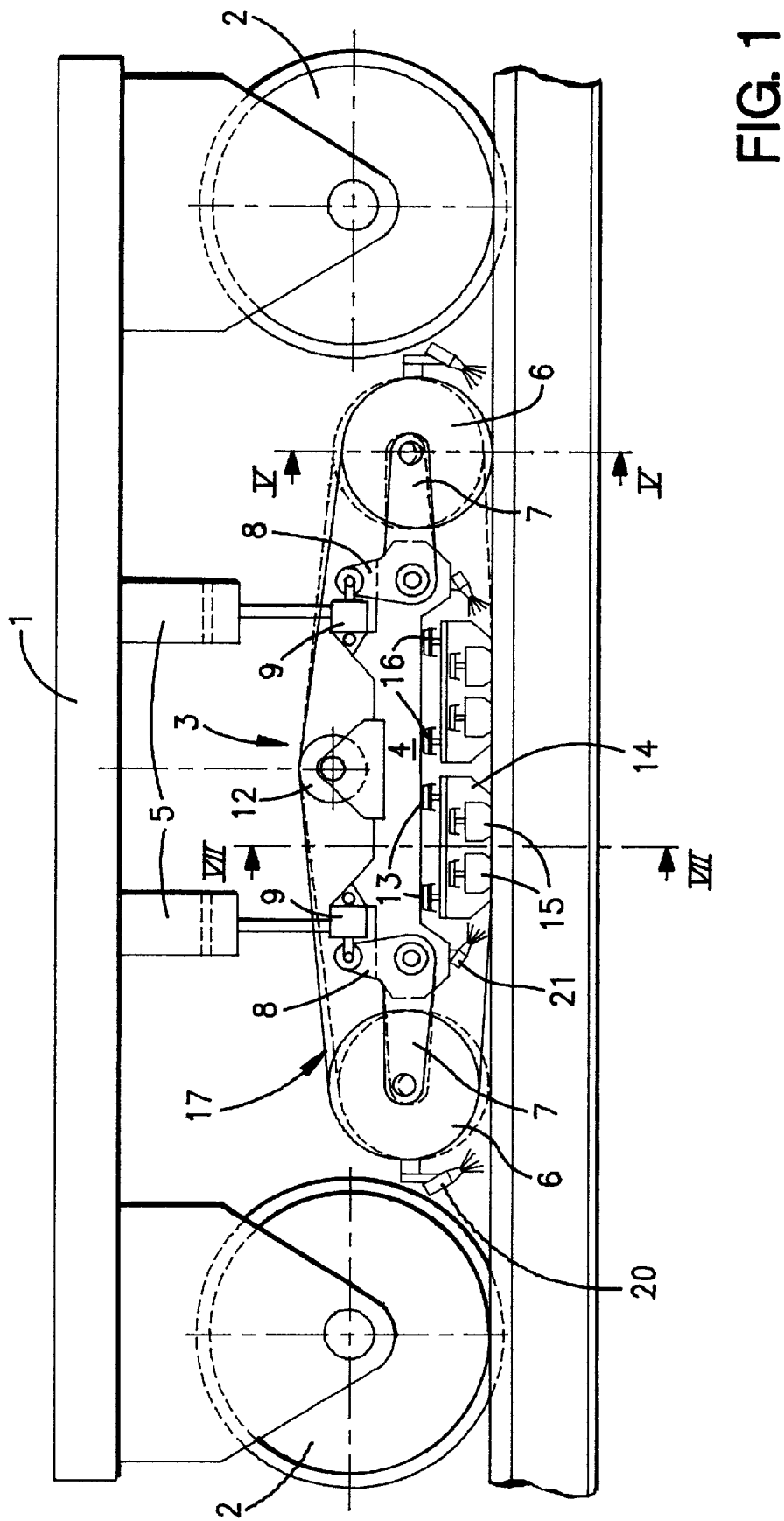
FIG. 1 is a schematic view of a support carriage designed for mounting beneath a railway vehicle, provided with a detection and/or measuring device according to the invention.

As will be apparent from the following detailed description, the new and original characteristic of this ultrasonic device for detecting and/or measuring the defects of a rail of a railway resides in the placing, between the sensor or sensors and the rail to be monitored, a web or a belt to prevent the direct contact of the sensors with the rail. This web can be made from a synthetic material, for example from a polyamide and have very smooth surfaces. This web is flexible, so that it can adapt to the undulations of the rail.

In one preferred embodiment described hereafter, the endless belt, forming a closed loop, passes between the sensors and the rail and thereafter is wound around rollers, and is further subjected to the action of a tensioning roller. In such an embodiment, when the railway vehicle carrying the measuring device moves along the railway, the part of the web located between the sensors and the rail acts like a track and does not move relatively to the rail, while the sensors slide on the smooth surface of the web. Obviously, means are provided for ensuring a good acoustic contact both between the sensors and the web, and between the web and the rail, for example by using water films.

The particular embodiment of the ultrasonic device illustrated and designed for detecting and/or measuring internal defects of a rail, includes a support carriage 1 running on the railway and arranged to be connected to a railway vehicle (not illustrated), generally to be mounted beneath the same and be pulled along the railway for detection or measurement purposes. This support carriage 1 can furthermore be connected to the underframe of the railway vehicle by lifting means to prevent the carriage from running on the railway when the same is not used, for example, between two sections of the railway selected for measuring or detection operations. One or several of these support carriages 1 can be placed under a railway vehicle, between bogies, and each one of these support carriages 1 is provided with flanged wheels 2 by means of which it runs and is guided along the railway.

Each support carriage 1 has at least one measuring carriage 3 for each one of the rails of the railway. These measuring carriages 3 include a frame 4 connected by two jacks 5 to the underframe of the support carriage 1, by means of which this measuring carriage 3 can be lowered into the operating position or lifted into the upper standby position.

The measuring carriage 3 has end rollers 6 rotating freely at the end of an arm 7 pivotally mounted on the frame 4 and including a connecting link 8 of which the end is connected by a double effect jack 9 to the frame 4. Thus, by actuating the jacks 9, it is possible to modify the height of the corresponding roller 6 relative to the frame 4 of the measuring carriage.

Each one of these rollers 6 (FIGS. 5, 6) includes a central part having a groove for receiving a band 10 made for example of rubber, for dampening the impacts transmitted by the rail when this roller presses against the rail. The lateral parts of the roller 6 are conical and can carry teeth 11.

The upper part of the frame 4 of the measuring carriage is provided with a tensioning roller 12 movable vertically relative to the frame 4, for example by means of a jack (not illustrated). The periphery of this tensioning roller 12 also carries teeth.

The lower part of the frame 4 is connected by means of a double effect jack 13 to measuring shoes 14 having each one two ultrasonic sensors 15.

Figure 2:
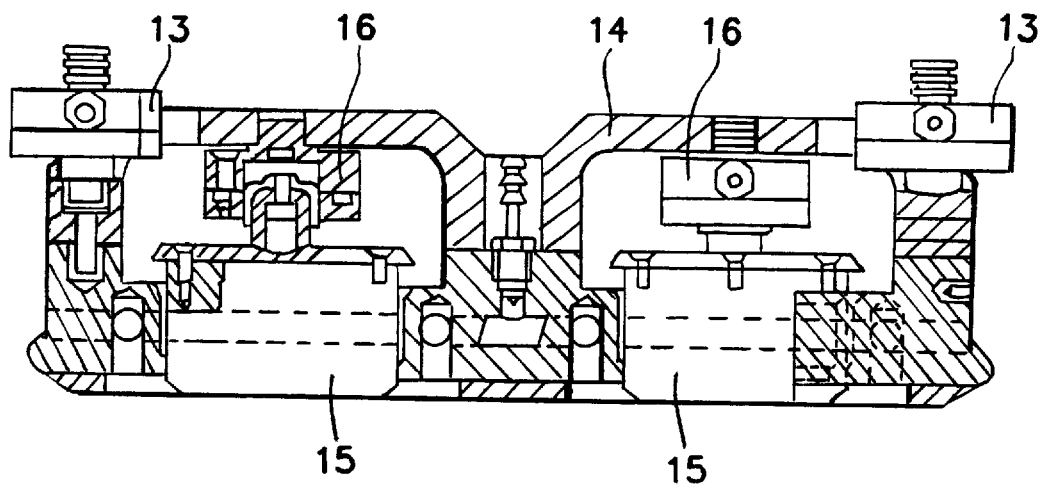
FIG. 2 is a cross-sectional view at an enlarged scale of a sensor carrying support of the device.
Figure 3:
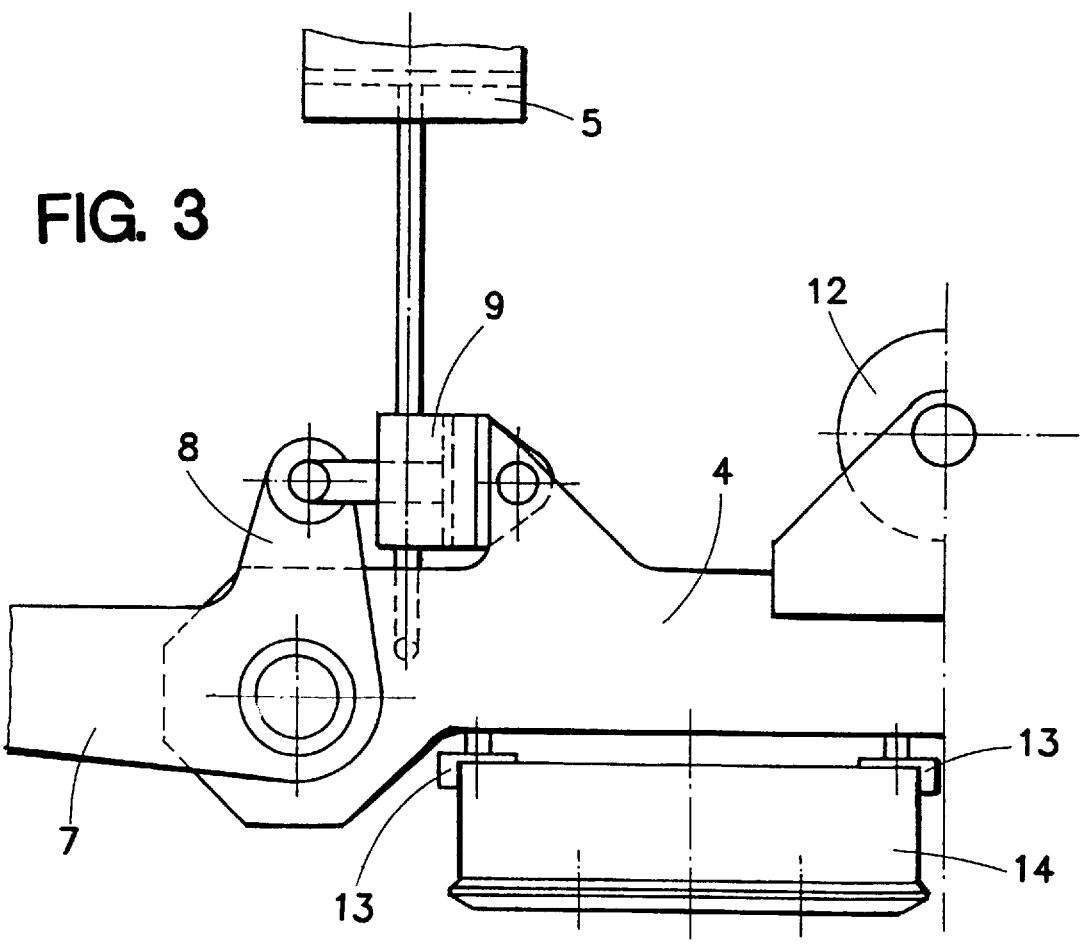
FIG. 3 is a partial view at an enlarged scale of the frame of the device.
Figure 7:
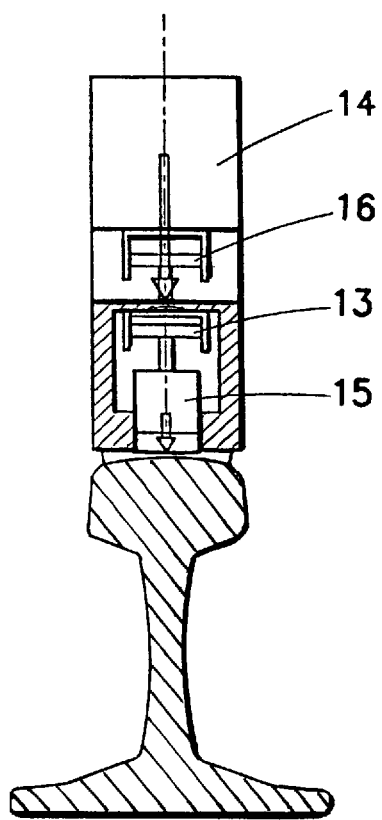
FIG. 7 is a cross-sectional view taken along line VII—VII of FIG. 1, at an enlarged scale.
Figure 8:
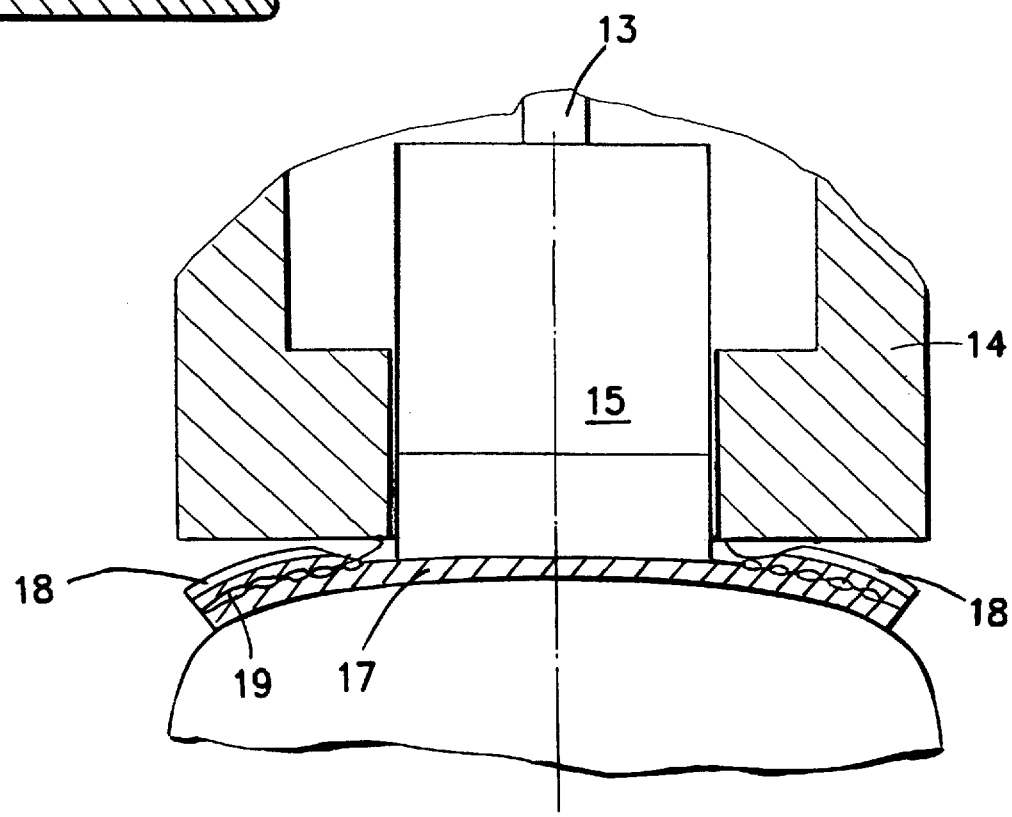
FIG. 8 is a detail of FIG. 7, at an enlarged scale.

Each measuring shoe 14 (FIG. 2) carries two sensors 15 mounted to slide along a vertical axis in the shoe and subjected to the action of a simple effect jack 16 acting as an impact damper. This shoe 14 can be provided with a water supply and recovery circuit to ensure the acoustic contact. These measuring shoes 14 will not be described in detail, since their construction and their functioning are object of the patents CH N° 1003/94, CH N° 3843/94 and U.S. Pat. No. 5,522,265.

To avoid the wear of the sensors 15 and to further reduce the impacts to which these sensors 15 are subjected, owing to the irregularities of the rail and the ends or connections of rail lengths, the present measuring carriage 3 is equipped with a smooth endless web 17 made of a synthetic material such as polyamide for example, which is pervious to ultrasounds and which is arranged under the lower surface of the sensors and runs around the rollers 6, 12. This endless web 17 carries in its two lateral portions serrated straps 18 incorporating cables or cords 19 preventing any extension of the web, the straps being attached by an adhesive, welding or in any other appropriate manner. These serrated straps 18 mesh with the teeth of the roller 12 and possibly of the rollers 6, to prevent any sliding motion of the web 17, as well as any transverse motion.

It is clear that in other versions, the serrations of the straps 18 could be made, for example, as pins cooperating with matching members on the rollers 12 and/or 6. Furthermore, these rollers can have lateral portions which are smooth.

During the measuring or the detection operation, the measuring carriage 3 is positioned in its lower position, and the web 17 comes in contact with the rail. The measuring shoes 14 are applied against the upper face of the web 17 with a force determined by the jacks 13 and the sensors 15 are maintained in contact with the smooth surface of the web 17 by the dampening jacks 16.

When the support carriage 1 is pulled along the railway, the web 17 remains applied against and in contact with the rail and the measuring carriage 3 advancing longitudinally moves the web 17 along the rail in the manner of a track and the sensors 15 slide on the smooth surface of the web 17, without bouncing back, being subjected to impacts or wear.

The front roller 6 is slightly lifted by its jack 9 and a water injection means 20 creates a liquid film between the web 17 and the rail to ensure a good ultrasonic contact. Also, the measuring carriage further includes means for injecting water between the web 17 and the measuring shoes 14 for ensuring a good acoustic contact. The latter means can be deleted when the measuring shoes 14 include an incorporated water injection system.

The main advantages of the ultrasonic measuring device described are the following:

a. The sensors do not rub against the rail, which has sometimes a rough surface, but against a closely fitting and highly smooth polyamide sheet and, accordingly, the wear of the sensors is practically nil.

b. The web acts as a cushion between the sensors and the rail, and the irregularities of the latter (for example undulations caused by wear, connections) are filtered and cause no vibration of the sensors.

c. The resulting quality and reliability of the measurements is substantially higher than that of former devices.

d. Furthermore, all the longitudinal or transverse movements, for example for the centering of the sensors, are possible as with previous devices, such as those described in patents EP 0374395 and U.S. Pat. No. 4,689,995.

e. The lifting of the front roller 6 makes it possible, on the one hand, to run smoothly over connections and, on the other hand, to properly lubricate the rail.

In other versions of the invention, it is possible to design the rollers 6 driving the web 17 be motor driven, to produce a motion of the web relative to the rail and to decrease the speed of motion of the sensors relative to the web. Such an arrangement can be advantageous for increasing the operational speed, while ensuring a good ultrasonic contact between the sensor and the rail through the web 17.

What is claimed is:

1. A device for continuously detecting in situ internal defects in a railway rail, the device comprising:
   a measuring carriage having an end roller at each end thereof and a tensioning roller therebetween;
   an endless web rotatably carried by said end rollers and tensioned by said tensioning roller, said web having a smooth interior surface and being pervious to ultrasounds; and
   a measuring shoe carried by said measuring carriage and having at least one ultrasonic sensor whose measuring surface is pressed against said smooth interior surface of said endless web opposite the rail when the device is positioned on the rail.

2. The device according to claim 1, wherein the device is mounted on a support carriage by means of jacks which move the device into an upper standby position or into a lower operative position, said support carriage for being connected to a railway vehicle.

3. The device according to claim 1, wherein said end rollers are pivotally mounted on said measuring carriage, so that said end rollers may be lifted relative to a plane of the rail.

4. The device according to claim 1, wherein said endless web has serrated straps at lateral portions thereof.

5. The device according to claim 4, wherein lateral portions of said end rollers carry teeth, and wherein said lateral portions of said end rollers are tapered outwardly and wherein a central portion of each of said end rollers carries a resilient band.

6. The device according to claim 5, wherein said serrated straps have cables therein.

7. The device according to claim 5, wherein said serrated straps cooperate with said teeth of said end rollers.

8. The device according to claim 4, wherein said end rollers rotate freely.

9. The device of claim 4, wherein said end rollers are rotatably driven.

10. The device of claim 1, further comprising means for providing a liquid film between said measuring surface and said smooth interior surface.

11. The device of claim 1, further comprising means for providing a liquid film on an exterior, rail contacting, surface of said endless web.

12. The device of claim 1, wherein said endless web comprises a synthetic material.

13. The device of claim 1, wherein said measuring shoe is supported by support jacks.

14. A device for continuously detecting in situ internal defects in a railway rail, the device comprising:

- a measuring carriage having rollers;
- an endless web rotatably carried by said rollers and whose exterior surface contacts the railway rail when the device is positioned on the rail; and
- at least one ultrasonic sensor whose measuring surface is pressed against an interior surface of said web opposite the rail when the device is positioned on the rail, so that said sensor avoids direct contact with the rail.

15. The device of claim 14, wherein said rollers rotate freely so that said exterior surface of the said web has no substantial speed relative to the rail when the device is moving along the rail.

16. The device of claim 14, wherein said rollers are rotatably driven so that said exterior surface of the said web has a speed relative to the rail when the device is moving along the rail.

\* \* \* \* \*